United States Patent [19]
Goldstein et al.

[11] Patent Number: 5,593,964
[45] Date of Patent: *Jan. 14, 1997

[54] METHOD OF TREATING SEPTIC SHOCK BY PREVENTING ACTIN POLYMERIZATION

[75] Inventors: Allan L. Goldstein, Bethedsa, Md.; Mirela O. Fagarasan, Washington, D.C.

[73] Assignee: The George Washington University Medical Center, Washington, D.C.

[*] Notice: The portion of the term of this patent subsequent to Oct. 10, 2014, has been disclaimed.

[21] Appl. No.: 292,757

[22] Filed: Aug. 18, 1994

Related U.S. Application Data

[63] Continuation of Ser. No. 132,902, Oct. 7, 1993, abandoned.

[51] Int. Cl.$^6$ ................................................ A61K 38/17
[52] U.S. Cl. .............................................. 514/12; 514/21
[58] Field of Search .................................. 530/301, 324; 514/12, 21, 921

[56] References Cited

U.S. PATENT DOCUMENTS

| | | | |
|---|---|---|---|
| 4,297,276 | 10/1981 | Goldstein et al. | 260/112.5 R |
| 4,395,404 | 7/1983 | Low et al. | 514/15 |
| 5,055,447 | 10/1991 | Palladino et al. | 514/12 |
| 5,260,224 | 11/1993 | Stossel et al. | 436/504 |
| 5,464,817 | 11/1995 | Stossel et al. | 514/2 |

OTHER PUBLICATIONS

Lee et al., New England Journal of Medicine vol. 326 pp. 1335–1341 (1992, May).
Safer, D. and Nachmias, V. T., *BioEssays*, 16:473–479 (1994).
Stossel, Thomas P., *The Machinery of Cell Crawling*, *Scientific American*, pp. 54–63 (Sep. 1994).
Ishitsuka et al., "Protective Activity of Thymosin Against Opportunistic Infections in Animal Models", *Cancer Immunology Immunotheraphy*, 14:3, pp. 145–150, Mar. 1983.
Ashkenazi et al., "Protection against endotoxic shock by a tumor necrosis factor receptor immunoadhesin", *Proc. Natl. Acad. Sci. USA*, 88:23, pp. 10535–10539, Dec. 1, 1991.

Watt et al., "Alterations in plasma levels and complexing of Gc (vitamin D–binding protein) in rats with endotoxic shock", *Biological Abstracts*, 88:7, Abstract No. 75029, 1989 (*Circ Shock*, 28:3, pp. 279–292, 1989).
Cross et al. Infection and Immunity vol. 61(7) pp. 2741–2747 (Jul. 1993).
Biotechnology Newswatch, Aug. 1, 1994 pp. 1 and 4.
Fitzer–Schiller, Washington Post, Jan. 19, 1993 p. D3.
Sawada et al., "Protection Against Infection with *Pseudomonas aeruginosa* by Passive Transfer of Monoclonal Antibodies to Lipopolysaccharides and Outer Membrane Proteins", *J. Inf. Dis.*, vol. 150, pp. 570–576 (1984).
Teng et al., "Protection Against Gram–negative Bacteremia and Endotoxemia With Human Monoclonal IgM Antibodies" *Proc. Nat'l Acad. Sci.*, vol. 82, pp. 1790–1794 (1985).
Baumgartner et al., "Association Between Protective Efficacy of Anti–Lipopolysaccharide (LPS) Antibodies and Suppression of LPS–Induced Tumor Necrosis Factor α And Interleukin 6", *J. Exp. Med.*, vol. 171, pp. 889–895 (1990).
Safer, D. et al, "Thymosin $\beta_4$ and $F_x$, An Actin–Sequestering Peptide, Are Indistinguishable," *J. Bio. Chem.*, vol. 266, pp. 4029–4032 (1991).
Sanders, M., et al. "Thymosin $\beta_4$ ($F_x$ Peptide) is a Potent Regulator of Actin Polymerization in Living Cells," Proc. Nat'l. Acad. Sci., vol. 89, pp. 4678–4682 (1992).
Webster's Third New International Dictionary, p. 1798 (1986).
Dorland's Illustrated Medical Dictionary, 26th ed., p. 1026 (not dated).
T. Low et al., "Thymosins: Structure, Function and Therapeutic Applications", *Thymus* 6, 27 42 (1984), pp. 27–42.

*Primary Examiner*—Jeffrey E. Russel
*Attorney, Agent, or Firm*—Rothwell, Figg, Ernst & Kurz

[57] ABSTRACT

A method of treating septic shock in a mammal by preventing in vivo polymerization of actin in the mammal. An actin antipolymerizer such as thymosin $\beta_4$ (T$\beta_4$) is administered to the mammal so as to treat septic shock in the mammal. The amount of T$\beta_4$ administered is sufficient to reduce levels of IL-1α, TNFα, PAF, Tx$\beta_2$ and/or 6-keto-PGF$_1$α in the blood of the mammal. Also disclosed is a method of preventing septic shock in a mammal following endotoxin introduction in the mammal by administrating an actin antipolymerizer such as T$\beta_4$.

9 Claims, No Drawings

METHOD OF TREATING SEPTIC SHOCK BY PREVENTING ACTIN POLYMERIZATION

This is a continuation of application Ser. No. 08/132,902, filed Oct. 7, 1993, now abandoned.

The present invention relates to a method of treating septic shock in mammals.

Description of Background Art

Septic shock is a condition in which infection is widely disseminated in many areas of the body, the infection generally being disseminated through the blood from one tissue to another and causing extensive damage. Septic shock can occur with numerous medical conditions, including (1) peritonitis caused by the spread of infection from the uterus and fallopian tubes; (2) peritonitis resulting from rupture of the gut, sometimes caused by intestinal disease or wounds; (3) generalized infection resulting from spread of a simple infection; (4) generalized gangrenous infection resulting specifically from gas gangrene bacilli; and (5) infection spreading into the blood from the kidney or urinary tract. Septic shock is of critical concern from a clinical viewpoint because, among other reasons, this condition frequently leads to death.

Although septic shock is a somewhat common clinical phenomenon, the mechanisms involved as well as the pathological changes remain poorly understood. For example, despite the treatment of bacterial infection, many patients deteriorate further, which may be due to clinical sequelae of hypotension with low systemic vascular resistance, renal insufficiency, adult respiratory distress syndrome, severe coagulopathy and severe metabolic dysfunctions. Thus, there is an urgent need in the art for effective methods of treating septic shock.

SUMMARY OF THE INVENTION

In accordance with the present invention, a method of treating septic shock in a mammal comprises preventing in vivo polymerization of actin in said mammal.

Description of the Preferred Embodiments

Actin is an abundant protein in mammals such as humans, with a central role in cell structure and motility. Following acute trauma and/or infection, G-actin (monomeric actin) is released into extracellular fluid and blood from damaged or dying cells and tissues. When G-actin is released from such cells and tissues, it has a strong tendency to polymerize to F-actin. The presence of filaments of F-actin in mammals can result in venous obstruction, pulmonary microthrombii and/or endothelial injury which can alter the characteristics of vascular flow in mammals. This alteration of vascular flow, in turn, can result in actin toxicity disorders.

It has been discovered that septic shock in a mammal can be treated or prevented by preventing polymerization of G-actin to F-actin in the mammal.

As used herein, the term "preventing polymerization" is intended to include the term "actin depolymerization". Additionally, the term "actin antipolymerizer" is intended to include actin depolymerizers, i.e., materials which depolymerize F-actin, as well as materials which prevent G-actin polymerization.

In accordance with one embodiment, a method of treating septic shock in a mammal comprises administering an effective amount of an actin antipolymerizer to said mammal.

One suitable actin antipolymerizer for use in accordance with the present invention in Thymosin $\beta_4$ ("T$\beta_4$"). Thymosin $\beta_4$ ("T$\beta_4$") is a peptide reported as containing 43 amino acids, which has been found to be present in numerous tissue types in mammals. Amino acid sequence information on T$\beta_4$ is disclosed in U.S. Pat. No. 4,297,276, herein incorporated by reference.

The terms "Thymosin $\beta_4$" and "T$\beta_4$" as used herein encompasses not only native (i.e., naturally occurring) T$\beta_4$ but also synthetic T$\beta_4$ and recombinant T$\beta_4$ having the amino acid sequence of native T$\beta_4$. The invention may also be applicable to biologically active amino acid sequences substantially similar to T$\beta_4$, or a biologically active abbreviated sequence form thereof, and their biologically active analogs (including muteins) having substituted, deleted, elongated, replaced, or otherwise modified sequences which possess bioactivity substantially similar to that of native T$\beta_4$.

Other actin antipolymerizers include profilin and gelsolin. As used herein, the terms "treating" and "treatment" are intended to include the terms "preventing" and "prevention". One embodiment of the present invention includes the administration of an actin polymerization-preventing amount of T$\beta_4$ to mammals.

According to one aspect of the present invention, when a septic shock treating-effective amount of an actin antipolymerizer such as T$\beta_4$ is administered to a mammal, the blood levels of pathological mediators of bacteria-induced lethality are decreased in the mammal. In accordance with this aspect, administration of an actin antipolymerizer such as T$\beta_4$ decreases the blood levels of arachidonic acid metabolites such as Tx$\beta_2$ and 6-keto-PGF$_1\alpha$, PAF, and cytokines such as IL-1$\alpha$ and TNF-$\alpha$.

The present invention is also applicable to treatment of actin toxicity disorders in which filaments of F-actin alter the characteristics of vascular blood flow in mammals. Such actin toxicity disorders include, but are not limited to, septic shock, acute respiratory disorder syndrome (ARDS), acute infection, hepatic necrosis, and certain disorders of pregnancy. Actin toxicity disorders in mammals are treated in accordance with the present invention by administering an effective amount of an actin antipolymerizer, such as T$\beta_4$, to the mammal.

According to preferred embodiments of the present invention, compositions containing an actin antipolymerizer such as T$\beta_4$ may be formulated in a conventional manner for administration by any suitable route. Suitable routes of administration include, but are not limited to, oral, rectal, nasal, topical, vaginal, and parenteral (including subcutaneous, intramuscular, intravenous and intradermal). Particularly preferred embodiments utilize oral or parenteral administration, with parenteral administration being a more preferred embodiment. It will be appreciated that the preferred route may vary with the condition, age and species of the recipient.

While not essential, in preferred embodiments, the actin antipolymerizer is administered as part of a pharmaceutical formulation. The formulations of the present invention comprise the actin antipolymerizer together with one or more pharmaceutically acceptable carriers and optionally with other therapeutic ingredients. The carrier(s) are "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and may be prepared by any suitable pharmaceutical methods.

Such methods include, but are not limited to, the step of bringing into association the actin antipolymerizer with the carrier which constitutes one or more accessory ingredients. In general, the formulations are prepared by uniformly and intimately bringing into association the actin antipolymerizer with liquid carriers or finely divided solid carriers or both, and then, if necessary, shaping the product.

Formulations of the present invention suitable for oral administration may be presented as discrete units such as capsules, cachets or tablets each containing a predetermined amount of the actin antipolymerizer; as a powder or granules; as a solution or a suspension in an aqueous liquid or a non-aqueous liquid; or as an oil-in-water liquid emulsion or a water-in-oil liquid emulsion, etc.

A tablet may be made by compression or molding, optionally with one or more accessory ingredients. Compressed tablets may be prepared by compressing in a suitable machine the actin antipolymerizer in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the actin antipolymerizer in a flavored basis, usually sucrose and acacia or tragacanth; pastilles comprising the actin antipolymerizer in an inert basis such as gelatin and glycerin, or sucrose and acacia; and mouthwashes comprising the actin antipolymerizer to be administered in a suitable liquid carrier.

Formulations suitable for topical administration to the skin may be presented as ointments, creams, gels and pastes comprising the actin antipolymerizer and a pharmaceutically acceptable carrier, or may utilize a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range from about 20 to about 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as tampons, creams, gels, pastes, foams or spray formulations containing, in addition to the actin antipolymerizer, suitable carriers.

Formulations suitable for parenteral administration include aqueous and non-aqueous sterile injection solutions which may optionally contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

It should be understood that in addition to the ingredients particularly mentioned above the formulations of this invention may include other suitable agents having regard to the type of formulation in question, for example, those suitable for oral administration may include flavoring agents.

When utilizing $T\beta_4$ as the antipolymerizer, a proposed dose for administration of the compositions in the present invention is an actin antipolymerizing amount of $T\beta_4$, which can be in a range of from about 0.4 to about 4 mg of $T\beta_4$ per kg of body weight of recipient (mg/kg), preferably from about 1 to about 4 mg/kg. A dose can be administered to the patient daily, one or more times per day of administration, e.g., two or three times per day, and doses can be administered one or more days per week, e.g., two, three, four, five, six or seven days per week.

In accordance with one embodiment of the present invention, an actin polymerizer such as $T\beta_4$ can be administered in combination with a therapeutically effective amount of another substance useful in treating septic shock such as, for example, antibiotics, or antibodies (polyclonal or monoclonal) directed to antigens located on endotoxins. Of course, the acceptable dosage range of the other substance will depend upon its properties (i.e., the acceptable dosage range will depend upon what other substance is being administered).

The actin antipolymerizer and another substance useful in treating septic shock can be administered "in combination" which, as defined herein, includes various schemes designed to administer the actin antipolymerizer and the other substance to a subject, whether or not the other substance and the actin antipolymerizer are administered separately or together, such that the desired dosages of the actin antipolymerizer and the other substance are present in the subject at the same time. Any suitable scheme can be used to administer the actin antipolymerizer and another substance useful in treating septic shock "in combination" in accordance with this aspect of the present invention.

Suitable dosages of either the actin antipolymerizer alone or the actin antipolymerizer in combination with another substance useful in treating septic shock may be administered 1 to 6 times or more per day. The precise dose administered will depend on the age, condition and other factors of the recipient.

The following examples are for illustrative purposes only, and are not to be construed in a limiting sense.

Example 1

Synthetic $T\beta_4$ was provided by Alpha 1 Biomedicals, Inc. (Two Democracy Center, 6903 Rockledge Drive, Ste. 1200, Bethesda, Md. 20817). $T\beta_4$ was prepared by solid phase peptide synthesis.

Swiss-Webster mice 4–6 weeks of age (20–25g) were housed 6 per cage. The mice were divided into 2 groups: endotoxic mice (endotoxin 60 mg/kg i.p. in acute treatment) and endotoxic mice treated with $T\beta_4$, 5 minutes and 2, 4, 6, 8, 10, 12, 14, 16, 18, 20, 22, 24 hours post administration of the endotoxin. Survival was recorded 2 times a day for 7 days. The results are presented in Table I below. As can be seen, $T\beta_4$ protected against lethal endotoxin shock and increased the survival rate to as much as 100%.

Example 2

Swiss-Webster mice 4–6 weeks of age (20–25g) were divided to the following 4 groups.
1. Mice treated with a lethal dose of endotoxin (60 mg/kg).
2. Mice treated with 60 mg/kg endotoxin followed by an injection of 100 μg T$\beta_4$ (5 minutes post administration of endotoxin).
3. Mice treated with 60 mg/kg endotoxin followed by 2 injections of 100 μg/T$\beta_4$ (immediately following and 2 hours post administration of endotoxin).
4. Mice treated with 60 mg/kg endotoxin followed by 3 injections of 100 μg T$\beta$4 (immediately following, 2 and 4 hours post administration of endotoxin).

The results are presented in Table I below. As can be seen, T$\beta_4$ administered 3 times post administration of endotoxin increased the survival rate of mice treated with endotoxin to 100%.

TABLE I

Survival of Swiss Webster Mice Following Lethal Endotoxin Dose and T$\beta_4$ (No. mice alive)

| Experimental Groups | 0 hrs | 24 hrs | 48 hrs | 72 hrs |
|---|---|---|---|---|
| Endotoxin 60 mg/kg | 7 | 1 | 1 | 1 |
| Endotoxin 60 mg/kg + T$\beta_4$ 100 μg 1x | 7 | 4 | 3 | 3 |
| Endotoxin 60 mg/kg + T$\beta_4$ 100 μg 2x | 7 | 4 | 4 | 4 |
| Endotoxin 60 mg/kg + T$\beta_4$ 100 μg 3x | 7 | 7 | 7 | 7 |

Example 3

Using the same materials and methods as in examples 1 and 2, the time and dose-dependency of the protective effect of T$\beta_4$ on endotoxin lethality were studied. The results are presented in Tables II and III below.

As can be seen in Tables II and III, T$\beta_4$ had a protective effect on endotoxin toxicity when given immediately following, 2 and 4 hours after endotoxin treatment. The most effective protective dose was 100 μg T$\beta_4$ administered three times. Also, T$\beta_4$ partially increased the survival of mice treated with endotoxin when it was administered three times in doses of 50 μg and 20 μg T$\beta_4$. 10 μg T$\beta_4$ has also sometimes shown positive activity.

TABLE II

Survival of Swiss Webster Mice Following Lethal Endotoxin Dose and T$\beta_4$ (No. mice alive)

| Experimental Groups | 0 hrs | 24 hrs | 48 hrs | 72 hrs | 96 hrs | 120 hrs |
|---|---|---|---|---|---|---|
| Endotoxin 60 mg/kg | 8 | 4 | 4 | 4 | 4 | 4 |
| Endotoxin 60 mg/kg + T$\beta_4$ 100 μg, 3x; T$\beta_4$ was administered immediately following, 2 and 4 hrs. after endotoxin. | 8 | 8 | 8 | 8 | 8 | 8 |
| Endotoxin 60 mg/kg + T$\beta_4$ 100 μg, 3x; T$\beta_4$ was administered 2, 4 and 6 hrs. after endotoxin. | 8 | 7 | 4 | 4 | 4 | 4 |
| Endotoxin 60 mg/kg + T$\beta_4$ 10 μg, 3x; T$\beta_4$ was administered immediately following, 2 and 4 hrs. after endotoxin. | 8 | 8 | 6 | 6 | 6 | 6 |

TABLE III

Survival of Swiss Webster Mice Following Lethal Endotoxin Dose and T$\beta_4$ (No. mice alive)

| Experimental Groups | 0 hrs | 24 hrs | 48 hrs | 72 hrs | 96 hrs | 5 days | 6 days |
|---|---|---|---|---|---|---|---|
| Endotoxin 60 mg/kg | 10 | 4 | 3 | 3 | 3 | 3 | 3 |
| Endotoxin 60 mg/kg + T$\beta_4$ 50 μg, 3x; i.p. T$\beta_4$ was administered immediately following, 2 and 4 hrs. after endotoxin. | 10 | 9 | 7 | 7 | 7 | 7 | 7 |
| Endotoxin 60 mg/kg + T$\beta_4$ 20 μg, 3x; i.p. T$\beta_4$ was administered immediately following, 2 and 4 hrs. after endotoxin. | 10 | 5 | 4 | 4 | 3 | 3 | 3 |
| Endotoxin 60 mg/kg + T$\beta_4$ 10 μg, 3x; i.p. T$\beta_4$ was administered immediately following, 2 and 4 hrs. after endotoxin. | 10 | 3 | 3 | 3 | 3 | 3 | 3 |

Example 4

Using the same methods and materials as in examples 1–3, the effect which T$\beta_4$ has on blood levels of IL-1$\alpha$, TNF-$\alpha$, PAG, Tx$\beta_2$ and 6-keto-PGF$_1\alpha$, which are pathological mediators of endotoxin induced lethality, was studied. The results are presented in Tables IV–IX below.

As can be seen in Tables IV–IX, T$\beta_4$ decreased IL-1$\alpha$, TNF-$\alpha$ serum levels as well as PAF, Tx$\beta_2$ and 6-keto-PGF$_1\alpha$ plasma levels after administration of a lethal dose of endotoxin.

TABLE IV

| EXPERIMENTAL GROUPS | IL-1$\alpha$ pg/ml (serum levels) | |
|---|---|---|
| | 1 hr | 3 hr |
| Endotoxin 60 mg/kg | 492 ± 45,2 | 550 ± 37,1 |
| Endotoxin 60 mg/kg + T$\beta_4$ 100 μg administered simultaneously | 147,5 ± 15,1 | 207,5 ± 19,3 |

TABLE V

| EXPERIMENTAL GROUPS | PAF (pg/ml) (plasma levels) | | | |
|---|---|---|---|---|
| | 0.5 hr. | 1 hr | 2 hr | 3 hr |
| Endotoxin 60 mg/kg | 78 ± 6 | 279 ± 17 | 127 ± 13 | 55 ± 3 |
| Endotoxin 60 mg/kg + T$\beta_4$ 100 µg administered simultaneously | 63 ± 7 | 161 ± 17 | 66 ± 5 | 46 ± 5 |

TABLE VI

| EXPERIMENTAL GROUPS | Tx$\beta_2$ (pg/ml) (plasma levels) | | | |
|---|---|---|---|---|
| | 0.5 hr. | 1 hr | 2 hr | 3 hr |
| Endotoxin 60 mg/kg | 1442 ± 103 | 2937 ± 258 | 912 ± 105 | 695 ± 65 |
| Endotoxin 60 mg/kg + T$\beta_4$ 100 µg administered simultaneously | 209 ± 9,5 | 607 ± 53 | 196 ± 18 | 112 ± 9 |

TABLE VII

| EXPERIMENTAL GROUPS | 6-keto-PGF1$\alpha$ (pg/ml) (plasma levels) | | | |
|---|---|---|---|---|
| | 0.5 hr. | 3 hr | 2 hr | 3 hr |
| Endotoxin 60 mg/kg | 341 ± 31 | 1141 ± 112 | 897 ± 75 | 811 ± 7 |
| Endotoxin 60 mg/kg + T$\beta_4$ 100 µg administered simultaneously | 141 ± 9 | 261 ± 23 | 147 ± 19 | 121 ± 13 |

TABLE VIII

| EXPERIMENTAL GROUPS | PAF (pg/ml) (serum levels) | | |
|---|---|---|---|
| | 1 hr | 3 hr | 5 hr |
| Endotoxin 60 mg/kg | 938 | 662 | 567 |
| Endotoxin 60 mg/kg + T$\beta_4$ 100 µg administered simultaneously | 807 | 591 | 496 |

TABLE IX

| EXPERIMENTAL GROUPS | TNF-$\alpha$ (pg/ml) (serum levels) | | |
|---|---|---|---|
| | 1 hr | 3 hr | 5 hr |
| Endotoxin 60 mg/kg | 938 | 662 | 567 |
| Endotoxin 60 mg/kg + T$\beta_4$ 100 µg administered immediately after endotoxin | 807 | 591 | 496 |

While the invention has been described and illustrated with details and references to certain preferred embodiments, those skilled in the art will appreciate that various modifications, changes, omissions, and substitutes can be made without departing from the spirit of the invention.

What is claimed is:

1. A method of preventing septic shock by protecting a mammal against endotoxin shock following endotoxin introduction in said mammal, comprising administering to said mammal an effective amount of an actin antipolymerizer to said mammal, so as to protect said mammal against endotoxin shock.

2. The method of claim 1 wherein said actin antipolymerizer is T$\beta_4$ in a sterile liquid carrier.

3. The method of claim 2, wherein the T$\beta_4$ is administered at a dosage from about 0.4 to about 4 mg per kg of body weight.

4. The method of claim 2, wherein the T$\beta_4$ is administered at a dosage from about 1 to about 4 mg per kg of body weight.

5. The method of claim 3, wherein the T$\beta_4$ is administered parenterally.

6. The method of claim 5, wherein the T$\beta_4$ is administered intravenously.

7. The method of claim 2, wherein the T$\beta_4$ is synthetic T$\beta_4$.

8. The method of claim 1, wherein the amount of actin antipolymerizer administered is sufficient to reduce an increase in levels in blood of said mammal of at least one member selected from the group consisting of IL-1$\alpha$ and TNF$\alpha$, wherein said increase in levels of said at least one member results from said endotoxin in said mammal.

9. The method of claim 1, wherein the amount of actin antipolymerizer admininstered is sufficient to reduce an increase in levels in blood of said mammal of at least one member selected from the group consisting of PAF, Tx$\beta_2$ and 6-keto-PGF$_1\alpha$, wherein said increase in levels of said at least one member results from said endotoxin in said mammal.

* * * * *